(12) United States Patent
Hammer et al.

(10) Patent No.: US 6,758,828 B2
(45) Date of Patent: Jul. 6, 2004

(54) CATHETER FOR CELL DELIVERY IN TISSUE

(75) Inventors: Bruce E. Hammer, Minnetonka, MN (US); Mark J. Conroy, St. Louis Park, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 219 days.

(21) Appl. No.: 10/013,636

(22) Filed: Dec. 10, 2001

(65) Prior Publication Data

US 2003/0109849 A1 Jun. 12, 2003

(51) Int. Cl.⁷ .................................................. A61M 3/00
(52) U.S. Cl. ........................ 604/43; 604/522; 604/93.01; 604/222
(58) Field of Search ........................ 604/23–26, 27–28, 604/43–45, 500, 506, 522, 93.01, 264, 272; 435/284.1, 325–326

(56) References Cited

U.S. PATENT DOCUMENTS

| | | | |
|---|---|---|---|
| 3,993,072 A | 11/1976 | Zaffaroni | 128/260 |
| 4,298,002 A | 11/1981 | Ronel et al. | 128/260 |
| 4,309,996 A | 1/1982 | Theeuwes | 128/260 |
| 4,391,909 A | 7/1983 | Lim | 435/178 |
| 4,475,916 A | 10/1984 | Himmelstein | 604/890 |
| 4,549,556 A | 10/1985 | Tarjan et al. | 128/785 |
| 4,673,566 A | 6/1987 | Goosen et al. | 424/19 |
| 4,689,293 A | 8/1987 | Goosen et al. | 435/1 |
| 4,800,898 A | 1/1989 | Hess et al. | 128/785 |
| 4,803,168 A | 2/1989 | Jarvis, Jr. | 435/240.22 |
| 4,806,355 A | 2/1989 | Goosen et al. | 424/424 |
| 4,892,538 A | 1/1990 | Aebischer et al. | 604/891.1 |
| 5,006,122 A | 4/1991 | Wyatt et al. | 606/130 |
| 5,104,403 A | 4/1992 | Brotzu et al. | 623/1 |
| 5,106,627 A | 4/1992 | Aebischer et al. | 424/424 |
| 5,107,847 A | 4/1992 | Knute et al. | 128/675 |
| 5,108,364 A | 4/1992 | Takezawa et al. | 604/43 |
| 5,113,868 A | 5/1992 | Wise et al. | 128/675 |
| 5,125,888 A | 6/1992 | Howard et al. | 600/12 |
| 5,171,217 A | 12/1992 | March et al. | 604/53 |
| 5,211,165 A | 5/1993 | Dumoulin et al. | 128/653.1 |
| 5,255,680 A | 10/1993 | Darrow et al. | 128/653.1 |

(List continued on next page.)

FOREIGN PATENT DOCUMENTS

| | | | |
|---|---|---|---|
| WO | WO 97/408871 | 11/1997 | .......... A61M/5/142 |
| WO | WO 98/07367 | 2/1998 | ............ A61B/5/00 |
| WO | WO 00/35531 | 6/2000 | ............ A61N/1/05 |

*Primary Examiner*—Loan H. Thanh
(74) *Attorney, Agent, or Firm*—Mark A. Litman & Associates, P.A.

(57) ABSTRACT

An apparatus delivers an agent to a treatment region, the apparatus having an outer cannula or lumen that has an internal surface and an external surface, the external surface being substantially smooth to penetrate tissue whereas the distal end is tapered; an inner cannula, or lumen coaxial to the outer cannula, providing a common fluid path (that is the same fluid passes through both the inner cannula and outer cannula) at the distal end with the inner surface of the outer cannula; a source of fluid to be passed through the common fluid path, the source of fluid comprising at least a reservoir of nutrients and/or gases for maintaining cells contained in a lumen coaxial and internal to the inner cannula; a semi-permeable membrane comprises the surface of the lumen, thus allowing controlled material transport across the lumen surface; a source of cells or other biologically active material mass flow connected to the proximal lumen so that the cells or other biologically active material can exit the distal portion upon entering the target tissue; and a first flow distributor located at the proximal end of the outer cannula to provide substantially uniform flow through the outer cannula.

18 Claims, 9 Drawing Sheets

U.S. PATENT DOCUMENTS

| | | | |
|---|---|---|---|
| 5,307,808 A | 5/1994 | Dumoulin et al. | 128/653.2 |
| 5,318,025 A | 6/1994 | Dumoulin et al. | 128/653.2 |
| 5,344,439 A | 9/1994 | Otten | 607/126 |
| 5,383,454 A | 1/1995 | Bucholz | 128/653.1 |
| 5,410,287 A | 4/1995 | Laskaris et al. | 335/216 |
| 5,487,739 A | 1/1996 | Aebischer et al. | 604/890.1 |
| 5,519,372 A | 5/1996 | Palkovich et al. | 335/216 |
| 5,554,148 A | 9/1996 | Aebischer et al. | 604/890.1 |
| 5,565,831 A | 10/1996 | Dorri et al. | 335/216 |
| 5,607,418 A | 3/1997 | Arzbaecher | 604/891.1 |
| 5,707,335 A | 1/1998 | Howard et al. | 600/12 |
| 5,713,357 A | 2/1998 | Meulenbrugge et al. | 128/653.2 |
| 5,715,822 A | 2/1998 | Watkins et al. | 128/653.5 |
| 5,720,720 A | 2/1998 | Laske et al. | 604/49 |
| 5,772,625 A | 6/1998 | Kruegger et al. | 604/9 |
| 5,779,694 A | 7/1998 | Howard | 604/891.1 |
| 5,800,392 A | 9/1998 | Racchini | 604/96 |
| 5,820,589 A | 10/1998 | Torgerson et al. | 604/93 |
| 5,821,011 A | 10/1998 | Taylor | 429/181 |
| 5,826,576 A | 10/1998 | West | 428/642 |
| 5,836,935 A | 11/1998 | Ashton et al. | 604/891.1 |
| 5,843,093 A | 12/1998 | Howard, III | 606/130 |
| 5,843,148 A | 12/1998 | Gijsbers et al. | 607/116 |
| 5,843,150 A | 12/1998 | Dreessen et al. | 607/116 |
| 5,858,009 A | 1/1999 | Jonkman | 604/264 |
| 5,861,019 A | 1/1999 | Sun et al. | 607/60 |
| 5,980,885 A | 11/1999 | Weiss et al. | 424/93.21 |
| 5,993,462 A | 11/1999 | Pomeranz et al. | 606/129 |
| 5,997,525 A | 12/1999 | March et al. | 604/508 |
| 6,030,358 A | 2/2000 | Odland | 604/27 |
| 6,180,059 B1 | 1/2001 | Divino, Jr. et al. | 422/45 |

CATHETER FOR CELL DELIVERY IN TISSUE

BACKGROUND OF THE INVENTION

1. Field of the Invention

The present invention relates to the field of medical devices, particularly to catheter medical devices, and to catheters for the delivery of cells to tissue in patients. More particularly, the present invention relates to catheters or delivery system designs to improve cell survivability during transportation and/or delivery.

2. Background of the Art

Oxygen is a crucial nutrient for human cells. Cell damage may result from oxygen deprivation for even brief periods of time, which may lead to organ dysfunction or failure. For example, heart attack and stroke victims experience blood flow obstructions or diversions that prevent oxygen from being delivered to the cells of vital tissues. Without oxygen, the heart and brain progressively deteriorate. In severe cases death results from complete organ failure. Less severe cases typically involve costly hospitalization, specialized treatments and lengthy rehabilitation.

Blood oxygen levels may be described in terms of the partial pressure of the oxygen dissolved in the blood ($O_2$). Typically, for arterial blood, normal blood oxygen levels (i.e., normoxia or normoxemia) range from 90–110 mm Hg. Hypoxemic blood (i.e., hypoxemia) is arterial blood with an $O_2$ less than 90 mm Hg. Hyperoxic blood (i.e., hyperoxemia or hyperoxia) is arterial blood with an $O_2$ greater than 400 mm Hg (see Cason et. al (1992), Effects of High Arterial Oxygen Tension on Function, Blood Flow Distribution, and Metabolism in Ischemic Myocardium, Circulation, Vol. 85, No. 2, pp. 828–838), but less than 760 mm Hg (see Shandling et al. (1997), Hyperbaric Oxygen and Thrombolysis in Myocardial Infarction: The "HOT MI" Pilot Study, American Heart Journal, Vol. 134, No. 3, pp. 544–550). Hyperbaric blood is arterial blood with an $O_2$ greater than 760 mm Hg. Venous blood typically has an $O_2$ level less than 90 mm Hg. In the average adult, for example, normal venous blood oxygen levels range generally from 40 mm Hg to 70 mm Hg.

In patients who suffer from acute myocardial infarction, if the myocardium is deprived of adequate levels of oxygenated blood for a prolonged period of time, irreversible damage to the heart can result. Where the infarction is manifested in a heart attack, the coronary arteries fail to provide adequate blood flow to the heart muscle. Treatment of acute myocardial infarction or myocardial ischemia often comprises performing angioplasty or stenting of the vessels to compress, ablate or otherwise treat the occlusion(s) within the vessel walls. For example, a successful angioplasty increases the size of the vessel opening to allow increased blood flow.

To reduce the risk of tissue injury typically associated with treatments of acute myocardial infarction and myocardial ischemia, it is usually desirable to deliver oxygenated blood or oxygen-enriched fluids to at-risk tissues. Tissue injury is minimized or prevented by the diffusion of the dissolved oxygen from the blood or fluids to the tissue and/or blood perfusion that removes metabolites and that provides other chemical nutrients.

Conventional methods for the delivery of oxygenated blood or oxygen-enriched fluids to at-risk tissues involve the use of blood oxygenators. Such procedures generally involve withdrawing blood from a patient, circulating it through an oxygenator to increase blood oxygen concentration, and then delivering the blood back to the patient. One example of a commercially available blood oxygenator is the Maxima blood oxygenator manufactured by Medtronic, Inc., Minneapolis, Minn.

There are drawbacks, however, to the use of a conventional oxygenator in an extracorporeal circuit for oxygenating blood. Such systems typically are costly, complex and difficult to operate. Often a qualified perfusionist is required to prepare and monitor the system.

Conventional oxygenator systems also typically have a large priming volume, i.e., the total volume of blood contained within the oxygenator, tubing and other system components, and associated devices. It is not uncommon in a typical adult patient case for the oxygenation system to hold more than one to two liters of blood. Such large priming volumes are undesirable for many reasons. For example, in some cases a blood transfusion may be necessary to compensate for the blood temporarily lost to the oxygenation system because of its large priming volume. Heaters often must be used to maintain the temperature of the blood at an acceptable level as it travels through the extracorporeal circuit. Further, conventional oxygenator systems are relatively difficult to turn on and off. For instance, if the oxygenator is turned off, large stagnant pools of blood in the oxygenator might coagulate.

Perhaps one of the greatest disadvantages to using conventional blood oxygenation systems is that the maximum partial pressure of oxygen ($O_2$) that can be imparted to blood with commercially available oxygenators is about 500 mm Hg. Thus, blood $O_2$ levels near or above 760 mm Hg cannot be achieved with conventional oxygenators.

U.S. Pat. No. 6,180,059 describes a system for the preparation and delivery of a gas-enriched fluid. In applications involving the prevention of ischemia or the treatment of ischemic tissues, the system may be used for the preparation and delivery of an oxygen-enriched fluid including blood to a specific location within a patient's body. The system may include a circuit for oxygenating or enriching blood, e.g., increasing the level of dissolved oxygen in the blood. The system includes an apparatus that combines a gas-supersaturated fluid with blood to form a gas-enriched fluid, advantageously for regional or localized delivery. The gas-supersaturated fluid may include an oxygen-supersaturated physiologic liquid, and the blood to be enriched is blood withdrawn from the patient. The system provided further includes assemblies for supplying controlled flows or supplies of the gas-supersaturated fluid and the blood. The system includes an elongated, generally tubular assembly including a central lumen and at least one end placeable within a patient body proximate a tissue site to be treated, the end including an outlet port for the gas-enriched fluid. The system may include a catheter defining a fluid pathway, including a proximal portion adapted for coupling to supplies of gas-supersaturated fluid and blood, and a distal portion defining a fluid pathway removably insertable within a patient's body, for infusing the gas-enriched fluid to predetermined sites.

U.S. Pat. No. 6,030,358 describes an apparatus for performing site specific microtherapy comprising a pump reservoir and one or more microcatheters dimensioned to be positioned within a tissue site for selectively removing fluids by microdialysis from the tissue'site, the microcatheter(s) being adapted for fluid communication with the pump reservoir to effect the recovery of fluid, the apparatus further comprising a delivery sheath adapted to be positioned into the tissue site, the microcatheter assembly adapted to be positioned within the delivery sheath, the delivery sheath having walls sufficiently permeable to permit a desired flow of fluids between the tissue and the microcatheter assembly in the course of microdialysis. A kit may comprise the apparatus wherein the microcatheter assembly comprises a plurality of microcatheters adapted to be positioned within the delivery sheath. The microcatheter assembly may be adapted to perform microdialysis based on size exclusion in order to remove tissue fluids and solutes based on solute size. The microcatheter assembly may also comprise a plurality of microcatheters, each in the form of a capillary tube having a lumen and semipermeable wall and the apparatus provides a plurality of fluid passageways.

Medical technology has advanced dramatically and swiftly over the past decades. The advances have been particularly significant within the fields of genetic engineering, cell technology, and in their proposed uses in actual therapies. For example, it is an increasingly common proposed medical technique to inject live cells into the human body. The intention of these cell implantation therapies (with genetically engineered cells or harvested cells) is to have the implanted cells attach to or settle into the tissues and provide their essential functions in their new location. The function of these therapeutic techniques may be to repair a genetic defect (producing a needed substance that the body is failing to create), repair traumatic damage, replace disease-diminished cells, contribute to the mechanical properties of an organ by the structures they build, and so forth. The science of cell implantation therapy is far in advance of the engineering technology needed to implement these therapies.

One engineering problem that is considered here is an appreciation of the fact that not all cells survive the injection process. When a substantial fraction of the cells fails to settle and function in the body, the efficacy of the treatment is much reduced. Although some cell deterioration is expected, there has been almost no consideration in the literature of this problem. There has been little publication on the design and engineering of delivery systems to reduce the impact of the delivery system on aggravating normal loss of viable cells.

U.S. Pat. No. 5,997,525 describes a system for delivering therapeutic or diagnostic agents to the heart, including a catheter that delivers the material to be delivered in a viscous carrier. The material may be delivered in association with an elongated, flexible transmission means for lasing that forms channels in the heart wall, as delivery locations.

U.S. Pat. No. 5,993,462 describes a shapeable catheter, which may include a pre-shaped region bent into a predetermined shape. A lumen may be proportioned to slidably receive a core wire. A pull wire may be provided to allow the user to cause deflection at a distal portion of the catheter.

U.S. Pat. No. 5,980,885 describes a method for inducing in vivo proliferation of precursor cells located in mammalian neural tissue. Simple glass pipettes are used to deliver the cell suspensions at levels of about 50,000 cell/microliter.

As can be seen from this review of the prior art, the delivery systems described tend to be essentially primitive tubes, with no consideration of flow functions or physical effects on cells during the delivery process. To assure that cell implantation becomes a viable procedure, it is essential that engineering considerations be used in the design of the pick-up, transportation and cell delivery devices.

Recent research suggests that improvements in cell delivery techniques may enhance the therapeutic efficacy of cell therapy. Multiple factors appear to influence long-term cell implant viability, including the site of the cell implant placement, the type of cells used in the implant, and the techniques used in the preparation of the cells to be transplanted. However, even when all of the above factors are taken into account, only 3–20% of implanted cells survive more than seven days. Membrane trauma and other related factors associated with the implantation process and cell delivery device appear to play a role in the high cell attrition rate. Improvements to the implantation methodology may be highly beneficial to increase cell survivability. Research data also indicate that the high attrition rate of transplanted cells may result from a lack of nutritive support due to inadequate local blood flow. Thus, there may be merit in using image-guided catheter devices to prepare and treat the tissue transplant area pre- and post operatively.

Recent research also indicates that optimal treatment of Parkinson disease (PD) patients may require that multiple locations within the brain be targeted for cell implants. At present, cell delivery over anatomically extensive regions of the brain involves multiple stereotactic probe placements, with concomitant invasion and damage to the overlying layers of healthy tissue. Additional catheter insertions may subsequently be required if nerve growth factors or other nutritive agents are to be infused. The development of a cell delivery device that reduces the number of insertion trajectories required for cell delivery could therefore significantly lower neurosurgical operating time and reduce surgical risk.

Targeted cell and drug delivery into the brain requires precise anatomic localization of normal and abnormal tissues. Present systems of image-guided placement of intracranial probes, such as drug delivery catheters, include framed and frameless technologies, which typically use images acquired preoperatively to create a three-dimensional space on which the surgical navigation is based. Framed systems use externally applied frames to establish the fiducials for navigation, whereas frameless systems use optical, electromagnetic, or ultrasound sensors and mechanical arms to track the position of surgical tools and instruments during surgical procedures.

The use of MRI to provide intraoperative imaging guidance is a relatively new concept made feasible by the development of new MRI systems that provide high spatial and temporal resolution imaging in conjunction with multiplanar and volumetric three-dimensional data acquisition, thereby making possible interactive image plane definition to facilitate surgical localization and targeting of a lesion and improving intraoperative navigation. Intraoperative MR imaging enables the surgeon to noninvasively visualize tissue planes beyond the surface of the tissue under direct evaluation during a clinical procedure. Moreover, MR imaging enables differentiation of normal from abnormal tissues, and it can display critical structures such as blood vessels in three dimensions. Thus, high-speed MR-guided therapy offers an improved opportunity to maximize the benefits of minimally invasive procedures in real-time.

MR imagers which permit continuous real-time visualization of tissues during surgical and endovascular procedures have already been developed. U.S. Pat. Nos. 5,410,287, 5,519,372, 5,565,831 and 5,713,357 provide illustrative examples of such systems. Newer generations of MR scanners provide frequently updated images of the anatomical structures of interest. This close to real-time imaging capability makes it possible to use high-speed MR imaging to observe the effects of specific interventional procedures, such as endovascular catheter tracking and intracranial administration of drug agents to targeted tissues, as disclosed by U.S. patent applications Ser. No. 08/857,043, Ser. No. 08/856,894, Ser. No. 08/916,596, Ser. No. 09/131,031, and Ser. No. 09/174,189.

Cell and drug delivery devices, such as catheters that are MR-visible, can be monitored by MR imaging, thus making intraoperative verification of catheter location possible during MR-guided procedures. U.S. patent application Ser. No. 08/857,043 describes a method for MR image-guided drug delivery. U.S. patent applications Ser. No. 08/856,894 and Ser. No. 08/916,596 disclose active MR visualization of catheters and other interventional probes by means of radiofrequency microcoils positioned at specific locations along the distal axis of the device. U.S. patent application Ser. No. 09/131,031 discloses a method and medical device for neurological interventions using nonlinear magnetic stereotaxis combined with MR imaging in order to perform image-guided targeted drug delivery in the brain. Alternative means of using MR signals to localize and track devices with small coils that are placed within the body are taught by U.S. Pat. Nos. 5,211,165, 5,307,808, 5,318,025 and 5,715,822.

Implantable miniature osmotic pumps, such as disclosed, by U.S. Pat. No. 4,475,916 to Himmelstein, et al. have been used to provide a continuous supply of drugs or other active biologic factors to the brain and other tissues at a controlled rate. Reservoir limitations as well as drug solubility and stability have, however, restricted the usefulness of this technology. Controlled sustained release of dopamine has been attempted from within bioabsorbable microcapsules, such as disclosed by U.S. Pat. Nos. 4,391,909 to Lim, U.S. Pat. Nos. 4,673,566, 4,689,293 and 4,806,355 to Goosen, et al., U.S. Pat. No. 4,803,168 to Jarvis and U.S. Pat. No. 4,883,666 to Sabel, et al. However, this method, appears to rely on surface erosion of the bioabsorbable polymer, which is in turn influenced by various hydrolytic events, thereby increasing the likelihood of drug degradation, and rendering predictable release rates difficult. A further problem appears to be attributable to limited diffusional surface area per unit volume of larger size microspheres, such that only a limited volume of cells can be loaded into a single microcapsule.

Exemplary of implantable microporous devices for drug delivery are U.S. Pat. No. 3,993,072 to Zaffaroni, U.S. Pat. No. 4,298,002 to Ronel et al., and U.S. Pat. No. 4,309,996 to Theeuwes. U.S. Pat. No. 5,104,403 to Brotsu, et al., discloses a vascular prosthesis with a low porosity outer material and a inner synthetic tubular mesh, in which semi-permeable microcapsules that contain hormone producing cells are placed between the outer material and the inner mesh, wherein blood flow through the vascular prosthesis allows for metabolism of the cells and circulation of the hormones. U.S. Pat. No. 5,171,217 to March, et al discloses a method for delivering drugs to smooth muscle cells lining blood vessels utilizing balloon catheter procedures and direct pressure delivery. However, unlike the present invention, the device patented by Brotsu, et al. does not disclose a method of MRI-guided intraparenchymal delivery and monitoring of cell therapy. U.S. Pat. No. 5,800,392 to Racchini describes a microporous balloon catheter for drug delivery where the catheter lumen is in fluid communication with the microporous balloon. This device is designed to deliver drugs and not contain or maintain cells. Fluid enters or exits the balloon via the catheter lumen and is not designed to have external flow circuits through the balloon. Furthermore, the catheter lumen wall is not formed by a microporous membrane.

Macroencapsulation, which generally involves loading cells into hollow fibers and then sealing the ends of the fibers, has also been used to deliver therapeutic drugs into the central nervous system. Exemplary of the macroencapsulation approach to drug delivery is U.S. Pat. No. 4,892,538 to Aebischer, et al., which discloses methods for delivery of a neurotransmitter to a target tissue from an implanted, neurotransmitter-secreting cell culture within a semipermeable membrane, wherein the surgically implanted cell culture device may be retrieved from the brain, replaced or recharged with new cell cultures, and re-implanted. U.S. Pat. No. 5,106,627 to Aebischer et al. additionally discloses a method for the combined delivery of neurotransmitters and growth factors from implanted cells encapsulated within a semi-permeable membrane. However, while these methods may offer the advantage of easy retrievability, the encapsulation of cells within macrocapsules implanted in the brain is often complicated by unreliable closure of the reservoir resulting in inconsistent results.

Studies utilizing implantation of cells capable of producing and secreting neuroactive factors directly into brain tissue have demonstrated that Parkinson's disease symptoms can be improved by transplanting fetal dopamine cells into the putamen of the brain of patients with Parkinson's disease. U.S. Pat. No. 5,487,739 to Aebischer, et al. discloses a cell therapy delivery method utilizing a cannula, obdurator, and implantable cells, wherein the biologically active factors diffuse into brain tissue through an implanted semipermeable membrane. U.S. Pat. No. 5,006,122 to Wyatt, et al. discloses an apparatus for transplanting tissue into a brain, comprising a stereotactic device for inserting a guide cannula to a target location within the brain into which a second cannula containing the tissue transplant is inserted and the tissue is deposited.

However, a major problem for this emerging therapy is the limited and variable supply of human fetal tissue and the societal issues associated with its use. Fetal pig neural cells have also been shown to survive in an immuno-suppressed parkinsonian patient. Improvements in the quality of transplantation also appear to be emerging. Recent studies, for example, Zawada, et al,. Nature—Medicine, Vol. 4, pps. 568–574 (1998) have demonstrated that somatic cell cloning can efficiently produce transgenic animal tissue for treating parkinsonism. It is also possible to surgically remove neural progenitor cells from a patient, grow the cells in culture, insert therapeutic genes, and then replace the transfected cells back into the patient's brain. However, the ability to monitor correct cell placement non-invasively with MR imaging is not currently available. Moreover, unlike the present invention, the previous studies and patented cell delivery methods may not permit non-invasive monitoring of the viability of the cells following their implantation into tissue.

Thus, there exists a need for an improved image-guided method to deliver cells that can produce biologically active factors to a target region of the brain. In addition, there is a need for a method to monitor non-invasively the ongoing viability of the cell implant, in particular to determine whether the cells are adequately perfused by the local microvasculature and continue to provide sustained and controlled delivery of the deficient biologically active factor.

Current methods of catheterization of the parenchymal tissues of the brain make it possible to measure intracranial pressure (U.S. Pat. No. 5,107,847), deliver drugs in a rate-controlled manner (U.S. Pat. No. 5,836,935), infuse various substances into the brain (U.S. Pat. No. 5,720,720), and convey fluids out of the brain (U.S. Pat. No. 5,772,625). U.S. Pat. Nos. 5,843,150 to Dreessen, et al, 5,861,019 to Sun, et al, 5,843,148 to Gijsbers, et al, 5,820,589 to Torgerson, et al, 5,821,011 to Taylor, et al., 5,826,576 to West, 5,858,009 to Jonkman, and PCT application WO9807367A1 to Jolecz, et al provide additional illustrative examples of such multi-probe systems.

Very recent technological developments are now leading to intraparenchymal catheterization systems that can be positioned within the brain by magnetic stereotaxis (U.S. Pat. Nos. 5,125,888; 5,707,335; 5,779,694), that are visible under magnetic resonance (MR) imaging (U.S. patent application Ser. No. 09/131,031), and that contain multi-purpose electrodes (U.S. Pat. No. 5,843,093). In addition, there are several types of implantable neurostimulator devices that have been disclosed. These include those described by Otten (U.S. Pat. No. 5,344,439), Hess, et al. (U.S. Pat. No. , 4,800,898), and Tarjan, et al. (U.S. Pat. No. 4,549,556) as three examples thereof.

U.S. Pat. No. 5,108,364 to Takezawa et al. discloses a monitoring catheter for medical use compressed of multiple tubes equipped for fluid delivery and removal, pressure measurement, and temperature measurement.

U.S. Pat. No. 5,113,868 to Wise et al. discloses a pressure sensing catheter system comprising a catheter, a pressure sensor, and a signal conduit Dumoulin et al., U.S. Pat. No. 5,255,680 to Darrow and Dumoulin, U.S. Pat. No. 5,307,808 to Dumoulin et al., and U.S. Pat. No. 5,318,025 to Dumoulin et al. additionally disclose a tracing system in which radiofrequency signals emitted by an invasive device, such as a catheter, are detected and used to measure the device's position and orientation in a patient. Localization of devices in situ is achieved by transmit radiofrequency coils positioned at its distal end, which are detected by receive radiofrequeney coils positioned around the imaging volume of interest. The position of the device, as determined by the tracking system, is superimposed upon independently acquired diagnostic images. U.S. Pat. No. 5,383,454 to Bucholz discloses a system for indicating a position of a tip of a probe which is positioned within an object on images of the object, wherein a computer employing transactional software translate the position of the tip of said probe into a coordinate system corresponding to the coordinate system of the cross-sectional images.

Each of the above-cited patents provide advantages and disadvantages for monitoring of physiologic parameters related to cell and drug therapy. However, none of the available methods of intraparenchymal catheterization can carry out multiple input-output functions at the same time with the same implanted device. Moreover, none of the above cited patents disclose a device and method means for targeted delivery of cells, with and without supportive intracranial drug therapy, as well as the monitoring of cell viability, as does the present invention. Also, none of the above cited patents disclose a method means for use of a device for acute and chronic delivery of cells into the human central nervous system during magnetic resonance (MR) imaging procedures, in particular during the injection or infusion of therapeutic stem cells into the brain parenchyma.

PCT WO97/40871 to Elsberry, et al. discloses an implantable pump and catheter for infusing drugs into the brain to treat movement disorders, wherein a sensor detects the symptoms resulting from the movement disorder and a microprocessor algorithm analyzes the output from the sensor in order to regulate the amount of drug delivered to the brain. U.S. Pat. No. 5,607,418 to Arzbaecher discloses an implantable drug delivery apparatus comprising a housing with a plurality of drug compartments which can be opened in a timed manner by a gas generating element to release the drugs into the tissue.

SUMMARY OF THE INVENTION

The present invention discloses a device and method means for intraparenchymal cell therapy, particularly during MR image-guided neurosurgical procedures, wherein the cells are provided with sufficient gases and a cell-safe transporting system to assist in maintaining cell viability during the therapy.

The operational characteristics of the present invention offer several conceptual and practical advantages over existing cell and drug delivery devices, which may be summarized as follows:

(a) The device disclosed by the present invention is designed to deliver cells into the brain with little or no damage to the cells. The cells are minimally affected by frictional drag forces along the catheter wall, by surface abrasion trapping on the inside surface of the catheter, and by thermal, mechanical and other forms of dynamic or hydrodynamic shock that might cause rupture of the cell membrane.

(b) The delivery device disclosed by the present invention has a geometry optimized to facilitate cell transport from a reservoir holding the cells through the interconnecting tubing into the catheter tip. In particular, the present device prevents "puddling" or any other form of aggregation of the cells throughout the flow conduit of the device.

(c) Cells may be per-loaded and cryopreserved in this device. Delivery of cells would entail warming the device and removing cryoprotectants by dialysis, in-situ, prior to injecting cells into target tissue.

(d) The device disclosed by the present invention causes little or no damage to the brain during insertion and removal. In particular, the outer coating of the catheter is lubricious and thereby minimizes 'drag' on brain tissues during insertion and removal.

(e) The design of the present device results in little or no reflux of the injection containing the cells during cell delivery and after withdrawal of the device from the brain.

(f) The tip of the present catheter device is visible on MRI to facilitate accurate placement of the device into target brain tissues. At the same time, MR imaging of the device in situ is free of imaging artifacts which could obscure accurate positioning of the catheter tip.

DETAILED DESCRIPTION OF THE INVENTION

Figure 1:
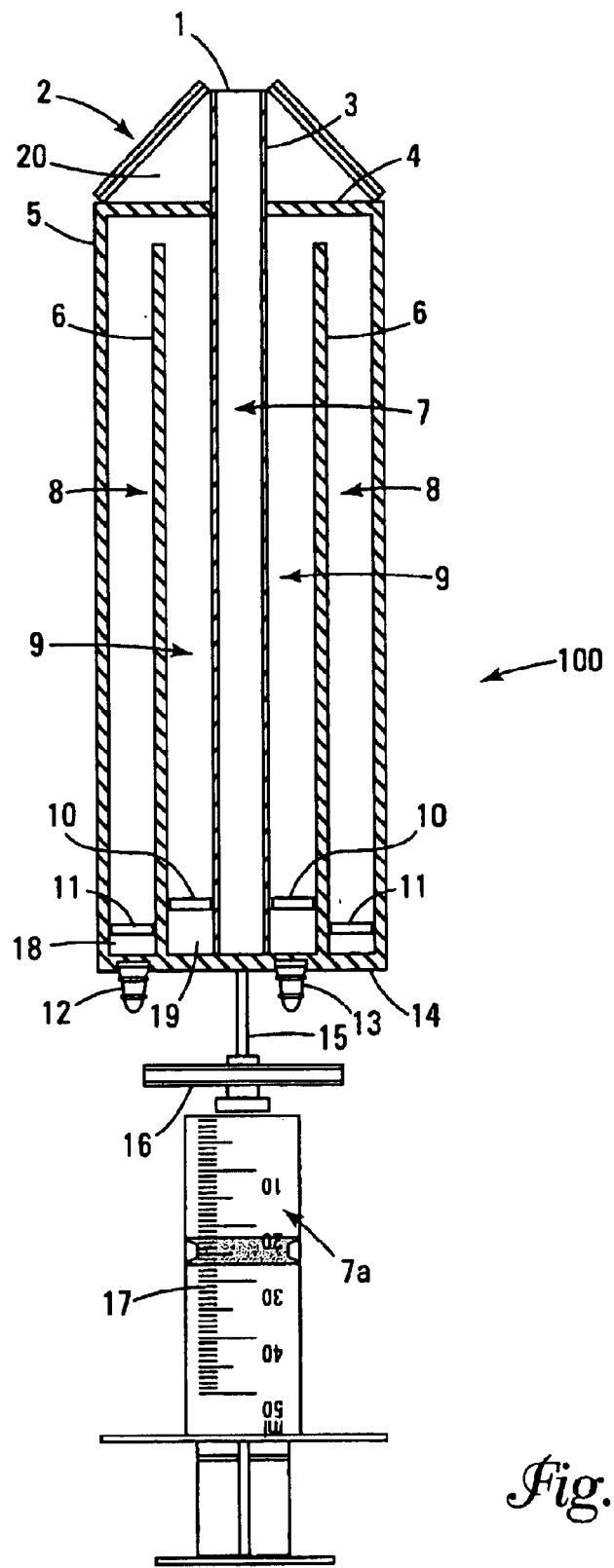
FIG. 1 is a side view of the delivery system demonstrating the integration of a semipermeable lumen coaxial with coaxial cannula for enhancing gas and metabolite transport to cells contained within the lumen.

One of the significant problems with direct cell delivery to living tissue is assuring that the cells remain metabolically viable and are accurately distributed to target tissue locations. Moreover, the efficacious delivery of therapeutic cells for the treatment of neurodegenerative diseases, as one example, requires that the cells be delivered as close to their target locations in the brain as possible, while minimizing increases in intracranial pressure during and after cell delivery. Cells delivered into the brain through implanted catheters will disperse from the site of injection at variable rates depending on a number of factors, including the physiochemical characteristics of the cells, size of the extracellular space, and geometry of the brain cell microenvironment. The degree to which each of these factors influences the distribution of a particular cell population may be an important determinant of the effectiveness of cell therapy for diseases of the central nervous system.

Although oxygen is needed for cell survival, hyperoxia can also cause damage to cells in culture or during transportation by causing oxygen stress. One objective of the perfusion catheter of the present invention is to assist in the control of physiological and physiochemical conditions so that collective damage (e.g., acidosis, anoxia, hyperoxia, shear damage, nutrient depravation, etc.) to the cells is minimized.

Furthermore, injection of a solution containing a macromolecular therapeutic drug agents into the intraparenchymal extracellular space of the brain may result in the injected drugs being sequestered as a cavity or depot. Ideally, the injected material infiltrates the extracellular space, and the subsequent tissue distribution of the drug is governed mainly by its molecular weight, molecular radius, and the tissue matrix structure into which the material has bee injected. However, if the injected drug solution instead forms a fluid-filled cavity in the tissue, this may lead to tissue swelling, an increase in ICP and, secondarily, altered interstitial transport of the drug solute.

The transport of an infused solute in swelling tissues has been described mathematically by Basser as:

$Pr=Q/4P_i r \ k$,

Where P=pressure at the exit of the catheter,

Q=flow rate, r=radial distance from the source, and k=hydraulic conductivity of the tissues It is, therefore, apparent that increases in ICP induced by intraparenchymal injections of liquid drug agents can injure tissues directly, or indirectly, by retarding the efficacious distribution of the drug due to tissue swelling and retarded interstitial solute transport. Thus, it is important to be able to monitor any local and regional increases in ICP resulting from injections of liquid drug agents directly into the brain parenchyma. The availability of an MR-visible drug delivery device which incorporates a method means for monitoring ICP would make it possible to obtain near real-time information on tissue pressure changes during interventional procedures in an intra-operative MR system.

The MR-visible cell delivery probe disclosed by the present invention can be navigated by magnetic stereotaxis (MSS) to the target tissue and/or advanced into the patient via endovascular, intracerebroventricular, or intraparenchymal entry ports based on real-time or near real-time MRI data, such as disclosed in U.S. patent application Ser. No. 09/131,031. Active MR visualization of the medical probe is achieved or enhanced by means of RF microcoils disposed along the distal axis of the probe, as disclosed by U.S. patent application Ser. No. 08/856,894 and Ser. No. 08/916,596. MR visibility can thereby be variably adjusted based on requirements related to degree of signal intensity change for probe localization and positioning, enhancement along the shaft of the probe, enhancement around the body of the probe, visibility of the proximal and distal ends of the probe, degree of increased background noise associated with probe movement, and other factors which either increase or suppress noise and artifacts associated with the probe.

An exemplary embodiment of the present invention will now be described with reference to the placement of the cell delivery probe into the brain of a patient with Parkinson's disease. Reference to the Figures will provide a better understanding of the practice and details of the present invention.

FIG. 1 shows a side view of a complete delivery system 100 according to the present invention. An exit port 1 from the cell transport lumen 3 of the system 100. The penetrating tip 2 is at the front of the system 100. A front containment facing 4 is provided inside of the system 100. A complete containment of transported materials is provided by an exterior cannula surface 5 and the rear containment facing 14. Within the exterior cannula surface is a second, interior cannula 6. The positioning and presence of the cell transport lumen 3, the second interior cannula 6 and the exterior cannula 5 define three distinct flow areas. Those three distinct flow areas comprise the cell flow region 7, an inner flow region 9, and an outer flow region 8. The exterior surface of the cell transport lumen 3 is transmissive of gas (such as oxygen) and low molecular weight materials that might be supportive of cell or biologically active material transported through lumen 3. Fluid transported through the inner flow region 9 allows material to pass, be transmitted or perfuse into the cell flow region 7. The nature of the flow within regions 8 and 9, determines certain attributes of the transfer of material into the cell flow region 7. For purposes of this discussion, oxygen will be assumed to be the material transferred, although as noted above, many various materials may be transported in zones 8 and 9, and may be transferred into the cell flow region 7.

Fluid flow within the inner flow region 9 and outer flow region 8 may be either flow from the inner flow region 9 to the outer flow region 8 (referred to as "co-current flow" as the flow through the inner flow region 9 would be parallel to the flow of cells within the cell flow region 7), or flow from the outer flow region 8 to the inner flow region 9 (which is referred to as "counter-current flow" as the flow of liquid within the inner flow region would be in an opposite direction to the flow of liquid within the cell flow region 7). Fluid flowing within the inner flow region 9 and outer flow region 8 would be introduced, respectively, at the rear flow distributor 10 of the inner flow region 9 or at the rear flow distributor 11 of the outer flow region 8 for co-current flow and counter-current flow. Nozzles 12 and 13 are provided for fluid introduction or fluid removal, with buffer or antisurge zones 18 and 19 provided. Cells (not shown) are provided into the system 100, for example, through a syringe system 17. The syringe system 17 is shown to comprise the syringe body 7a, the needle tip 15, and collar 16.

Figure 2:
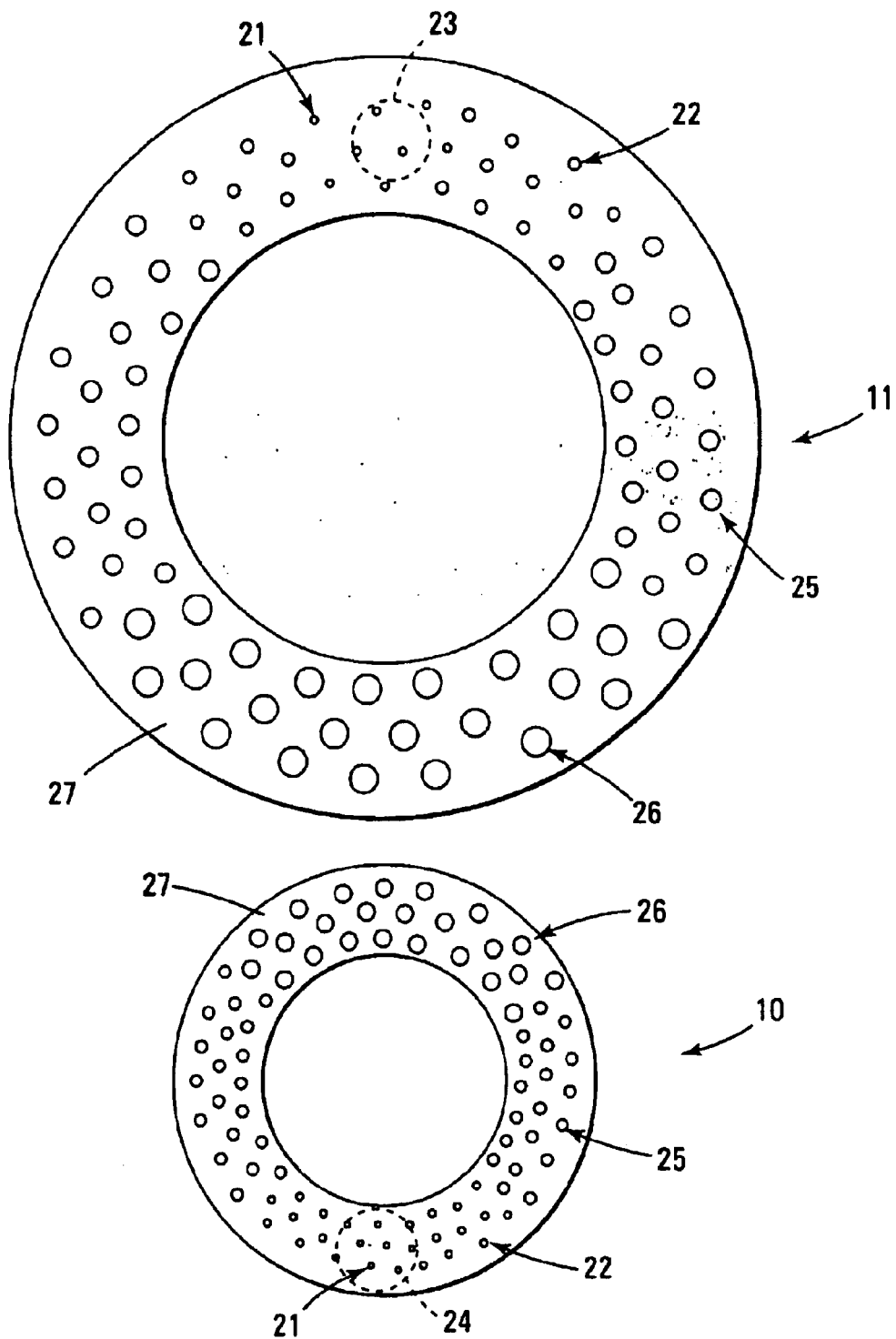
FIG. 2 is a top view of flow distributors for the inner and outer cannulas.

FIG. 2 shows two flow distributors 10 and 11 having structural material 27 defining the annulus of the distributors 10 and 11, with holes 21, 22, 25, and 26 of different sizes to cause internal liquid flow patterns to assure that material to be passed through a semipermeable membrane between the inner flow region and the cell flow region within the cell flow lumen is maintained at a consistent level within the liquid within the inner flow region. Regions 23 and 24 identify regions on the distributors 10 and 11 where liquid is introduced to the distributer through nozzles 12 and 13.

Figure 3:
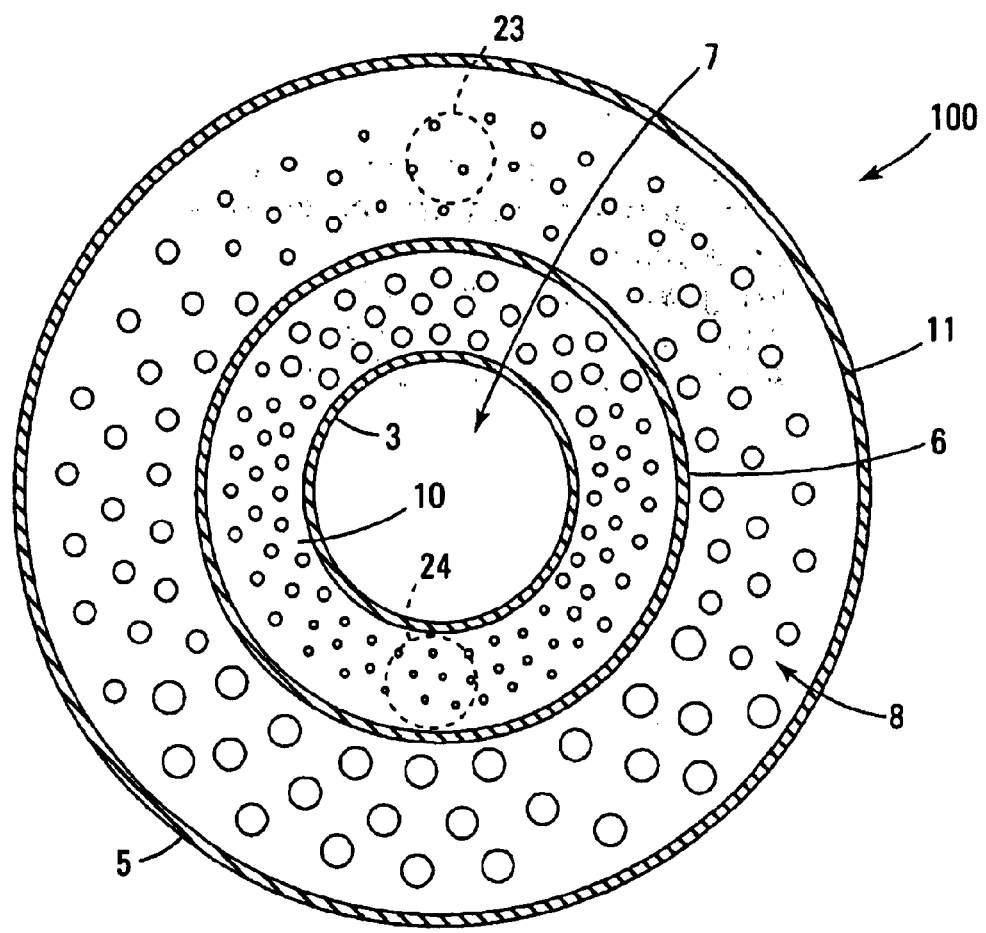
FIG. 3 is a cross section of the delivery system at the level of the flow distributor.

FIG. 3 shows a cross-section of the inlet region of the cell delivery system 100, with the outer cannula surface 5, the inner cannula surface 6, the cell flow tube 3, the outer flow region 8, the inner flow region 9, and the cell flow region 7 shown. Regions 23 and 24 identify the location of inlet/outlet nozzles, 12 and 13, above the distributors 10 and 11.

Figure 4:
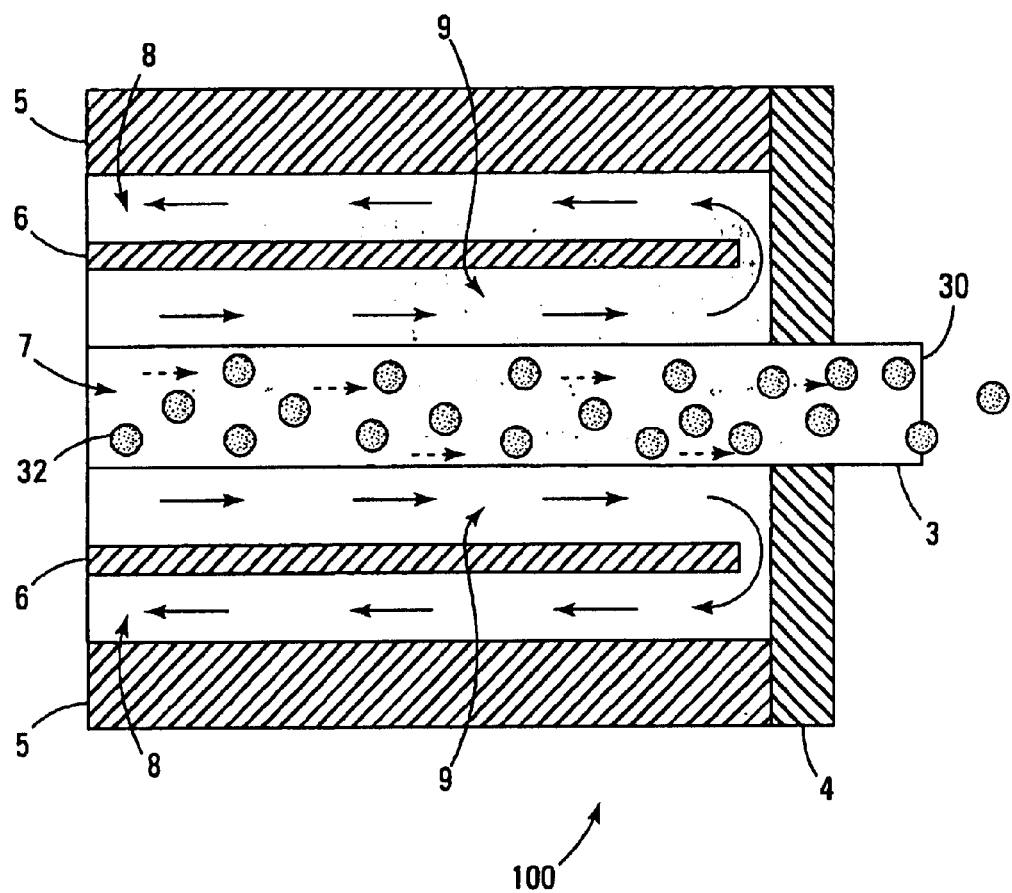
FIG. 4 is a side view of the delivery device demonstrating fluid dynamics when flow along the outside of the cell containing lumen is the same direction as flow within the lumen.

FIG. 4 shows a cutaway side view of the delivery end 30 of the cell delivery system 100 in a co-current flow pattern. Flow patterns of liquid within flow regions 8 and 9 are shown as arrows. The flow pattern of cells 32 in the cell flow area 7 is also shown by arrows.

Figure 5:
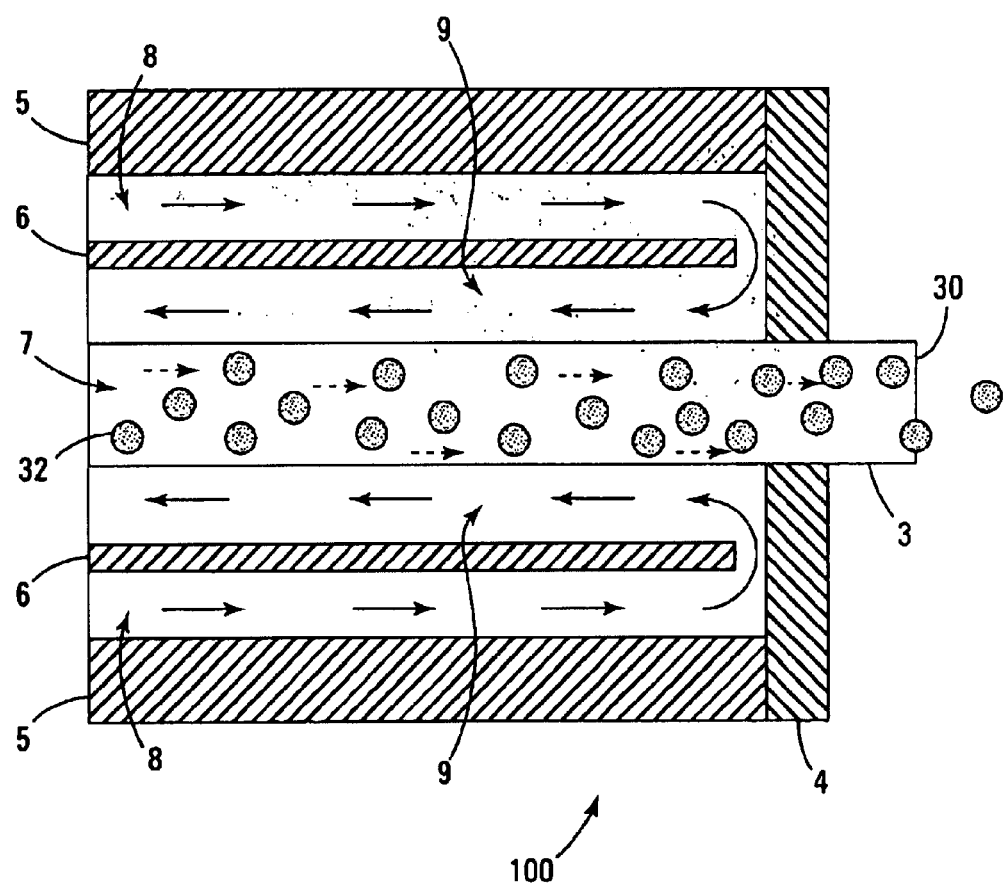
FIG. 5 is a side view of the delivery device demonstrating fluid dynamics when flow along the outside of the cell containing lumen is the opposite direction as flow within the lumen.

Similarly, FIG. 5 shows counter-current flow within interior and exterior liquid flow regions 9 and 8. The flow pattern of cells 32 in the cell flow area 7 is also shown by arrows. The tendency of counter-current flow is to provide the highest oxygen or metabolite content fluid towards the delivery end of the cell delivery system, as oxygen or metabolites will pass through the semipermeable surface 45 of the cell flow tube structure and into the liquid medium flowing within the cell flow area 7.

Figure 6:
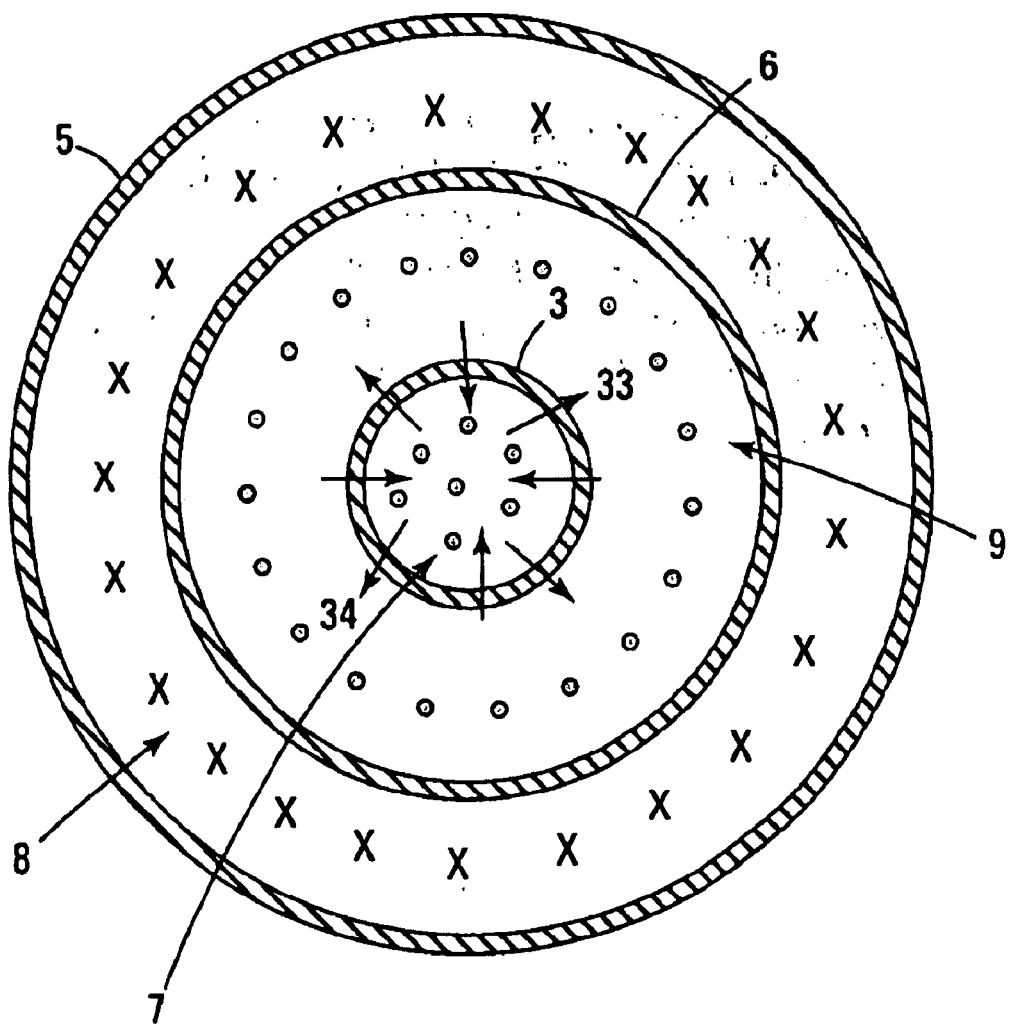
FIG. 6 is a cross sectional view of the flow pattern during co-current flow within the delivery device.

FIG. 6 shows an end view cross-section of flow patterns for co-current flow within the delivery device.

Figure 7:
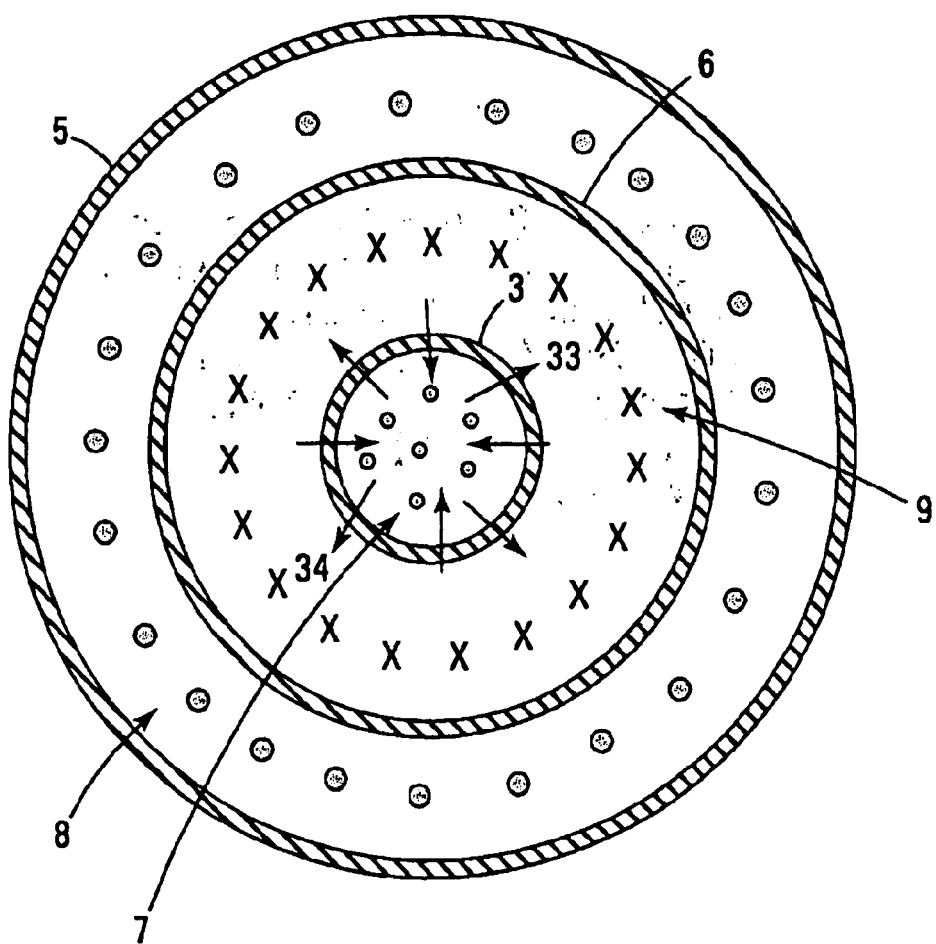
FIG. 7 is a cross sectional view of the flow pattern during counter-current flow within the delivery device.

FIG. 7 shows an end view cross-section of flow patterns for counter-current flow within the delivery device.

Figure 8:
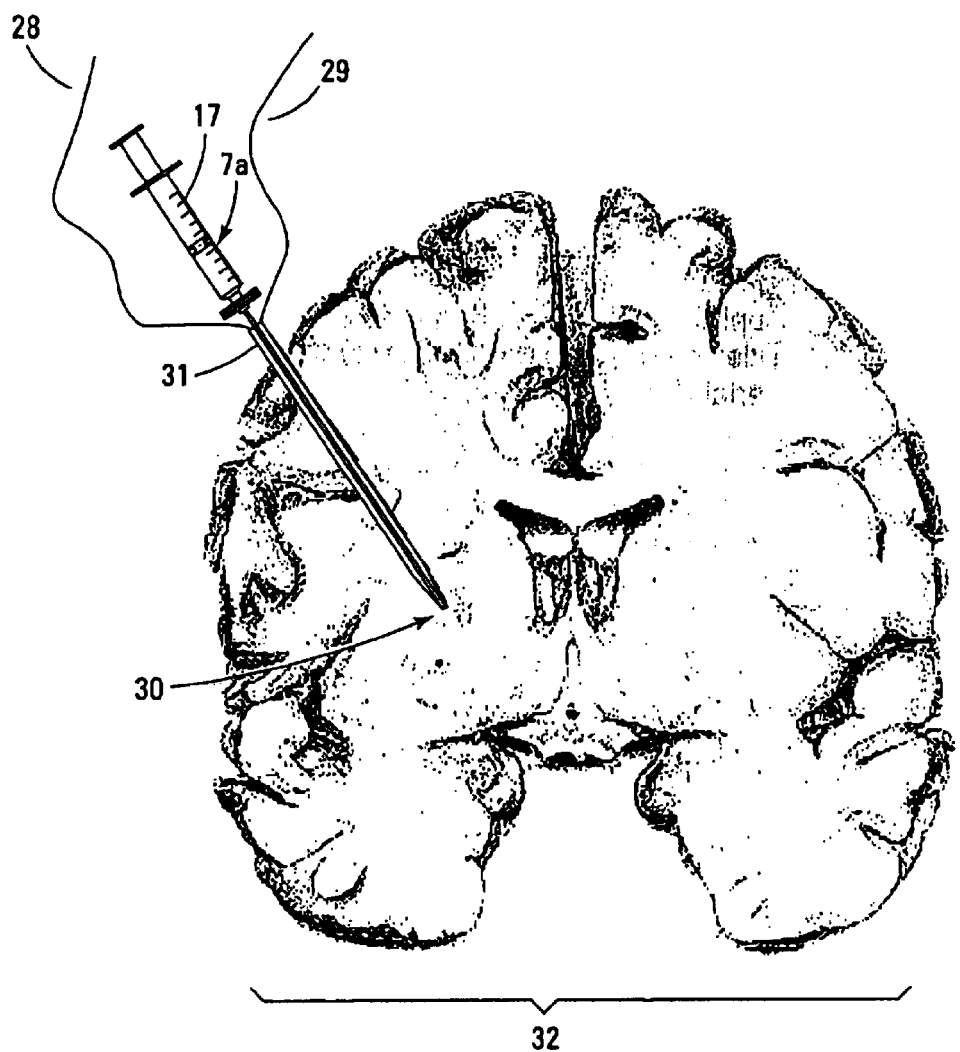
FIG. 8 is a side view of the delivery device in accordance with one embodiment of the present invention delivering an active agent to the putamen region of human brain.

FIG. 8 shows a cross-section of a brain 32 into which cells are being delivered by a delivery system 17 of the invention. Two electronic wires 28 and 29 are shown to assist in sensing or other operational functions within the device. The wires 28 and 29 may be attached to RF coils, thermally sensitive couplings, microelectronic devices, micromechanical devices, chemical sensors, or the like.

In the preceding detailed description of the preferred embodiments, references made to the accompanying drawings which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that structural, logical, physical, architectural, and electrical changes may be made without departing from the spirit and scope of the present invention. The preceding detailed description is, therefore, not to be taken in a limiting sense, and the scope of the present invention is defined only by the appended claims and their equivalents.

The dimensions of the components of the device may vary depending upon the intended use of the device, as different areas of a patient may tolerate delivery devices of differing dimensions. For example, line 80 may include four 100 micron inner diameter by 350 micron outer diameter tubes, for instance, potted together with epoxy at their proximal and distal ends. However, the inner diameter may be in the range of about 20 to about 1000 microns, with an inner diameter of about 100 to about 125 microns being particularly advantageous. Of course the exact size and shape of the distal end and tip of line 80 may vary depending upon the circumstances involved in a particular application. Examples of possible configurations include, without limitation, flat, blunt, squared, pencil-shaped, curved, parabolic, hyperbolic, and pyramidal.

Cells to be delivered from the transporting/delivery system of the invention may be effected by perfusion or direct (e.g., injected) delivery. The cells may driven by a pressure gradient through the lumen, which may contain a semipermeable membrane. The pressure gradient moves or drives the cells from the proximal end to distal end of the catheter. Mechanical elements (e.g., fans, diastolic movement of a sheath, and the like), fluid movement or gas movement pushing the cells can generate the pressure gradient.

The use of a semipermeable membrane allows for facile transfer of proteins, gases and waste products to and from cells contained in the fiber lumen. A semipermeable hollow fiber may be located inside of a concentric tube that has a cell-free fluid that continually flows past and around the hollow fiber. The cell-free medium contains the necessary metabolites and gases to ensure cell viability and these metabolites and gases are transferred across a non-barrier separating system (e.g., semi-permeable membrane, controlled diffusion barrier, etc.). The cell-free media can comprise any supporting medium that will not itself damage the metabolites or react with the gases. For example, the cell-free media may contain perfluorodated hydrocarbons to enhance oxygen solubility. The cell-free media can also be used to dialyze cryoprotectant compounds when the catheter is pre-loaded with frozen cells. Under these conditions the catheter device is warmed to where cells in the lumen and syringe are no longer frozen. The cryoprotective agents are then dialyzed from the cells which effectively removes cryoprotectants from the cell system prior to tissue injection. This is important because cryoprotective agents can damage cells in the target tissue.

As noted above, flow in the chamber concentric to the hollow fiber can be co-current or counter current to the direction of cell movement in the hollow fiber lumen. That is, the direction of cell-free media flow adjacent to the outside wall of the hollow fiber can flow from proximal to distal or from distal to proximal. The choice of flow direction depends on the application. A counter current flow, i.e., distal to proximal, will expose cells at the distal end of the catheter to higher oxygen and nutrient levels. This is where cells would normally be most nutrient and oxygen deprived (FIG. 1). Co-current, i.e., proximal to distal flow, is also possible (FIG. 4).

Cells will be normally ejected from the hollow fiber through an orifice that is large enough to assure passage of the cells without damaging the cells as they exit the orifice. The orifice opening should be greater than 1.0 cell diameters, preferably greater than 1.1 maximum cell diameters, up to 20 cell diameters or more. This larger opening reduces shear stress and should enhance viability. Because cells can be maintained for long periods of time within the delivery device, cell ejection from the lumen can be quite slow, thereby further minimizing shear stress.

Excess fluid injected into the targeted interstitial tissue may result in an increase of extracapillary fluid pressure. This may damage normal cells in the host and possibly the newly infused cells. Hollow fibers located in this vicinity, operating with a hydrostatic pressure gradient such that the interstitial tissue pressure exceeds that at the end of the hollow fiber will effectuate a decrease in extracellular or interstitial fluid pressure. This should further relieve cell stress. By controlling the fluid pressure in the transport lumens, and assuring that exit pressure from the lumen in the region of the target tissue, cell stress can be reduced.

Therefore, interstital fluid pressure should be determined or estimated in advance of treatment, and the exit pressure (the pressure within the last 1.0 to 2.0 mm of the delivery tube leading to the orifice, should be maintain at a pressure that is 1) less than or equal to the interstitial tissue pressure, 2) equal to the interstitial pressure, or 3) equal to or within a range no more than 1.0%, 0.5% or 0.2% above the interstitial pressure in the target area. The general range must be at least equal to or greater than the ambient extrastitial fluid pressure surrounding the target tissue (or the fluid and cells would not exit from the orifice) and no more than a pressure that would damage cells because the exiting pressure would so greatly exceed the interstitial tissue pressure that cells of the tissue would be damaged, for example, no more than 1.0% in excess of the interstital pressure.

Figure 9:
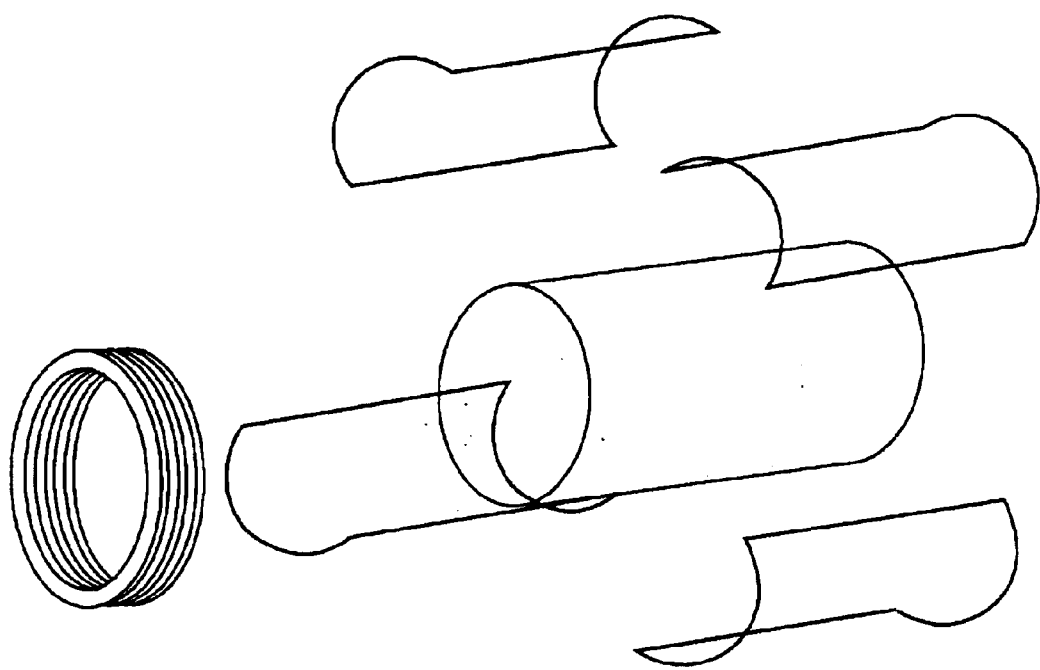
FIG. 9 shows an exploded view of a Three Coil Phase Array.
Figure 9:
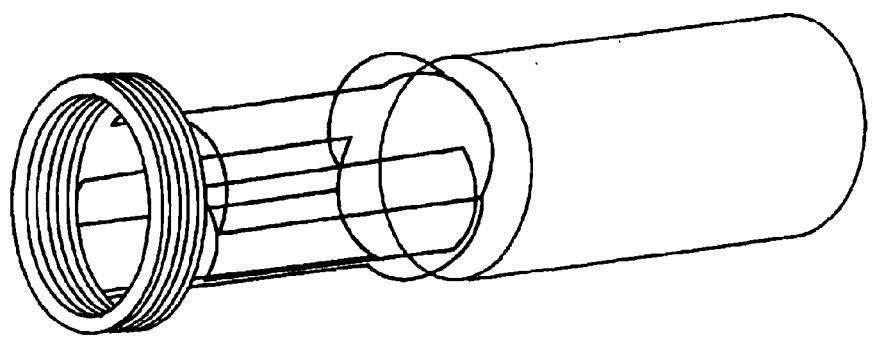

A three coil concentric phased array is shown in FIG. 9 to consist of two transverse Helmoltz saddle coils 103 and one solenoid coil 105 (FIG. 9). The transverse coils are most sensitive to tissue and fluids lateral to the catheter device. The distal end solenoid coil is most sensitive to tissue and fluids in front of the catheter. Cells are driven by a pressure gradient through the lumen that contains a semipermeable membrane. The semipermeable membrane allows for transfer of proteins, gases and waste products to and from cells contained in the fiber lumen. Measuring elements, such as near infrared sensors and emitters (e.g., NIR) may be present within the catheter or subcomponents may be used to measure or detect physiologic or physiochemical conditions. For example, NIR may measure a redox state of Fe in Hb, thereby yielding the level of tissue/cell oxygenation. This type of data may be fed through a data feed (e.g., fiber optic element, conductive wire, etc.) to an external receiver. The receiver may be a measuring device (e.g., directly measuring current that is translated into data, such as a temperature) or a data processing device (e.g., microprocessor or computer) to analyze and interpret data. NIR may also be used to measure a redox state of Cu in Cytochrome a,a3 which correlates with the level electron transport and ATP formation. This is an indicator of cell viability that can be used to adjust therapy, as by adjusting active ingredient content (e.g., oxygen, metabolites, nutrients) or conditions (e.g., temperature, flow rate, local pressue, pressure gradient, etc.).

The invention may be variously described as an apparatus for delivering an agent to a treatment region, whereas the apparatus comprises:

an outer cannula or lumen that has an internal surface and an external surface, the external surface being substantially smooth to penetrate tissue whereas the distal end is tapered an inner cannula, or lumen coaxial to the outer cannula, providing a common fluid path (that is the same fluid passes through both the inner cannula and outer cannula) at the distal end with the inner surface of the outer cannula, a source of fluid to be passed through the common fluid path, the source of fluid comprising at least a reservoir of nutrients and/or gases for maintaining cells contained in a lumen coaxial and internal to the inner cannula, a semipermeable membrane comprises the surface of the lumen, thus allowing controlled material transport across the lumen surface, a source of cells or other biologically active material mass flow connected to the proximal lumen so that the cells or other biologically active material can exit the distal portion upon entering the target tissue, a first flow distributor located at the proximal end of the outer cannula to provide substantially uniform flow through the outer cannula, a second flow distributor located at the proximal end of the inner cannula to provide substantially uniform flow through the inner cannula, a fluid path from the proximal end to the distal end along the outer surface of the semipermeable lumen to facilitate mass transport between the cell or active material within the lumen and the reservoir.

The apparatus may also having a repository for waste products and gases from cells or other biologically active materials contained in the lumen coaxial and internal to the inner cannula.

The delivery device may further comprise:

a proximal fitting to insert fluid to the outer cannula a proximal fitting to remove fluid from the inner cannula a fitting to pass the active agent from proximal to distal region of the device.

The delivery device may also further comprise:

a proximal fitting to remove fluid from the outer cannula a proximal fitting to insert fluid to the inner cannula a fitting to pass the active agent from proximal to distal region of the device The distal tip may be at an acute angle. The lumen may contain a semipermeable membrane. For example, the membrane material may comprise a polymer such as a polysulfone, molecular sieve or other polymer for controlling molecular weight cutoff. The lumen may contain or transport any form of cell, by way of non-limiting examples, cells that secrete an active biological factor or fetal stem cells for treatment of Parkinson's disorder. The fluid in the cannula may contain cytokines, nutrients, dissolved gases and other compounds necessary for maintenance of cell viability within the lumen.

The delivery device may have a portion in the tip where no material transport occurs through the semipermeable membrane of the lumen to prevent over-oxygenation of biologically active compound. The delivery device may have an outer cannula comprising a low friction material for insertion into target tissue FIG. 9 shows an exploded view of a three-coil phase array, with opposed coils 1, 1 and 2, 2 and tip 3.

A method for delivering cells to target location in a subject according to the invention may, for example, comprise:

(i) surgically defining an access hole in proximity to treatment site;

(ii) inserting a cell delivery system comprising an at least dual lumen cannula through tissue whereas the distal end of the cannula is at the treatment site, a first lumen carrying cells and a second lumen carrying metabolite or gas that may pass from the first lumen to the second lumen;

(iii) passing fluid through the second lumen to nourish and/or remove waste products from cells in the first lumen;

(iv) passing cells and its support medium through the first lumen containing a semipermeable membrane by hydrostatic pressure;

(v) maintaining a flow rate of cells through the first lumen at a rate consistent with minimizing shear forces to said cells;

(vi) maintaining cells within the lumen with oxygenation and nutrient supply from the second lumen;

(vii) maintaining cell delivery by flowing cell-free media through the first lumen;

(viii) removing cell delivery system from the treatment site.

The method may use a lumen in the cell delivery device removes waste products while cells are delivered. The method may be optimized for the delivery of cryopreserved cells in a process comprising:

(i) removing the delivery device from an environment where cells and fluids are substantially frozen prior to inserting the cannula through tissue whereas the distal end of the cannula is at the treatment site;

(ii) passing fluid through at least the second lumen to nourish cells and remove both metabolic and cryoprotective waste products from cells in the first lumen, (iii) allowing cells to thaw within the delivery device;

(iv) passing cells and its support medium through the first lumen containing a semipermeable membrane by hydrostatic pressure;

(v) maintaining the flow rate of cells through the lumen at a rate to minimize shear forces to said cells;

(vi) maintaining cells within the lumen with oxygenation and nutrients from the second lumen;

(vii) maintaining cell delivery by flowing cell-free media through the lumen; and (viii) removing the cell delivery system from the treatment site.

In this method, a lumen in the cell delivery device removes waste products while cells are delivered.

Another way of describing a method according to the invention for delivering a biologically active compound or cell to target location in a subject with a material delivery device having one lumen for delivery of cells to a target site and having two opposed lumens, the two opposed lumens comprising a distal direction flow lumen and a proximal direction flow lumen, the method comprising:

1) surgically defining an access hole in proximity to treatment site;

2) inserting the delivery device through tissue whereas the distal end of the delivery device is at the treatment site;

3) passing cell supportive fluid through the two opposed lumens to nourish cells and remove waste products from cells in the first lumen;

4) passing cells and its support medium through the first lumen containing a semipermeable membrane by hydrostatic pressure;

5) whereas the flow rate of cells through the lumen is maintained at a rate to reduce shear forces to said cells;

6) maintaining cells within the lumen with oxygenation and nutrients, and removal of waste products, during the delivery process;

7) maintaining cell delivery by flowing cell-free media through the lumen; and 8) removing cell delivery system from the treatment site.

The method may have flow of cell supportive liquid through the two opposed lumens so in a counter-current or co-current mode.

What is claimed is:

1. An apparatus for delivering an agent to a treatment region, whereas the apparatus comprises:

(i) an outer cannula that has an internal surface and an external surface, the external surface being substantially smooth to penetrate tissue whereas the distal end is tapered (ii) an inner cannula, coaxial to the outer cannula, providing a common fluid path at the distal end with the inner surface of the outer cannula, (iii) a source of fluid to be passed through the common fluid path, the source of fluid comprising at least a reservoir of nutrients and gases for maintaining cells contained in a lumen coaxial and internal to the inner cannula, (iv) a semipermeable membrane comprises the surface of the lumen, thus allowing transport across the lumen surface, (v) a source of cells or other biologically active material mass flow connected to the proximal lumen so that the cells or other biologically active material can exit the distal portion upon entering the target tissue (vi) a first flow distributor located at the proximal end of the outer cannula to provide substantially uniform flow through the outer cannula (vii) a second flow distributor located at the proximal end of the inner cannula to provide substantially uniform flow through the inner cannula (viii) a fluid path from the proximal end to the distal end along the outer surface of the semipermeable lumen to facilitate mass transport between the cell or active material within the lumen and the reservoir.

2. The apparatus of claim 1 also having a repository for waste products and gases from cells or other biologically active materials contained in the lumen coaxial and internal to the inner cannula.

3. The apparatus of claim 1, further comprising (i) a proximal fitting to insert fluid to the outer cannula (ii) a proximal fitting to remove fluid from the inner cannula (iii) a fitting to pass the active agent from proximal to distal region of the device.

4. The apparatus of claim 3 further comprising:

(i) a proximal fitting to remove fluid from the outer cannula (ii) a proximal fitting to insert fluid to the inner cannula (iii) a fitting to pass the active agent from proximal to distal region of the device.

5. The apparatus of claim 1, wherein the distal tip is of an acute angle.

6. The apparatus of claim 5, wherein there is a portion in the tip where no transport occurs through lumen of semipermeable membrane to prevent over-oxygenation of biologically active compound.

7. The apparatus of claim 1, wherein the lumen contains a semipermeable membrane.

8. The apparatus claim 7, wherein the membrane material comprises of polysulfone or other polymer for controlling molecular weight cutoff.

9. The apparatus of claim 8, wherein the lumen contains fetal stem cells for treatment of Parkinson's disorder.

10. The apparatus of claim 7, wherein the lumen contains cells that secrete an active biological factor.

11. The apparatus of claim 1, wherein fluid in the cannula contains cytokines, nutrients and other compounds necessary for maintenance of cell viability within lumen.

12. The apparatus of claim 11, wherein the fluid contains dissolved gases necessary for cell viability.

13. The apparatus of claim 1, wherein the outer cannula comprises a low friction material for insertion into target tissue.

14. A method for delivering cells from the delivery device of claim 1 to a target location in a subject comprising:

a) surgically defining an access hole in proximity to treatment site;
b) inserting a cell delivery system comprising an at least dual lumen cannula through tissue whereas the distal end of the cannula is at the treatment site, a first lumen carrying cells and a second lumen carrying metabolite or gas that may pass from the first lumen to the second lumen;
c) passing fluid through the second lumen to nourish and/or remove waste products from cells in the first lumen;
d) passing cells and its support medium through the first lumen containing a semipermeable membrane by hydrostatic pressure;
e) maintaining a flow rate of cells through the first lumen at a rate consistent with minimizing shear forces to said cells;
f) maintaining cells within the lumen with oxygenation and nutrient supply from the second lumen;
g) maintaining cell delivery by flowing cell-free media through the first lumen;
h) removing cell delivery system from the treatment site.

15. The method of claim 14 wherein a lumen in the cell delivery device removes waste products while cells are delivered.

16. A method for delivering a biologically active compound or cell to target location in a subject with a material delivery device according to claim 1 having one lumen for delivery of cells to a target site and having two opposed lumens, the two opposed lumens comprising a distal direction flow lumen and a proximal direction flow lumen, the method comprising:
a) surgically defining an access hole in proximity to treatment site;
b) inserting the delivery device through tissue whereas the distal end of the delivery device is at the treatment site;
c) passing cell supportive fluid through the two opposed lumens to nourish cells and remove waste products from cells in the first lumen;
d) passing cells and its support medium through the first lumen containing a semipermeable membrane by hydrostatic pressure;
e) whereas the flow rate of cells through the lumen is maintained at a rate to reduce shear forces to said cells;
f) maintaining cells within the lumen with oxygenation and nutrients, and removal of waste products, during the delivery process;
h) maintaining cell delivery by flowing cell-free media through the lumen; and
l) removing cell delivery system from the treatment site.

17. The method of claim 16 wherein flow of cell supportive liquid through the two opposed lumens so in a counter-current mode.

18. The method of claim 16 wherein flow of cell supportive liquid through the two opposed lumens so in a co-current mode.

* * * * *